United States Patent
Otsuka et al.

(10) Patent No.: US 12,072,330 B2
(45) Date of Patent: Aug. 27, 2024

(54) METHOD FOR CLASSIFYING/COUNTING LEUKOCYTES, REAGENT KIT FOR CLASSIFYING LEUKOCYTES, AND REAGENT FOR CLASSIFYING LEUKOCYTES

(71) Applicant: SYSMEX CORPORATION, Kobe (JP)

(72) Inventors: Saori Otsuka, Kusatsu (JP); Kazuki Hatcho, Kobe (JP); Toshihiro Mizukami, Kobe (JP); Shinichiro Oguni, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 74 days.

(21) Appl. No.: 16/915,851

(22) Filed: Jun. 29, 2020

(65) Prior Publication Data

US 2020/0326332 A1 Oct. 15, 2020

Related U.S. Application Data

(60) Division of application No. 14/061,333, filed on Oct. 23, 2013, now abandoned, which is a continuation of application No. PCT/JP2012/060432, filed on Apr. 18, 2012.

(30) Foreign Application Priority Data

Apr. 28, 2011 (JP) ................................ 2011-101595

(51) Int. Cl.
| | | |
|---|---|---|
| G01N 33/50 | (2006.01) | |
| G01N 15/14 | (2006.01) | |
| G01N 15/1429 | (2024.01) | |
| G01N 21/49 | (2006.01) | |
| G01N 21/64 | (2006.01) | |
| G01N 15/01 | (2024.01) | |

(52) U.S. Cl.
CPC ..... *G01N 33/5094* (2013.01); *G01N 15/1429* (2013.01); *G01N 15/147* (2013.01); *G01N 21/49* (2013.01); *G01N 21/6428* (2013.01); *G01N 2015/011* (2024.01); *G01N 2015/016* (2024.01)

(58) Field of Classification Search
CPC ....... G01N 33/5094; G01N 2015/0069; G01N 21/49; G01N 15/1429; G01N 15/147; G01N 21/6428; G01N 2015/008; G01N 2015/011; G01N 2015/016
See application file for complete search history.

(56) References Cited

U.S. PATENT DOCUMENTS

| | | |
|---|---|---|
| 5,538,893 A | 7/1996 | Sakata et al. |
| 2007/0298408 A1 | 12/2007 | Mizukami et al. |
| 2009/0023129 A1 | 1/2009 | Xu et al. |
| 2010/0151509 A1 | 6/2010 | Ting et al. |

FOREIGN PATENT DOCUMENTS

| | | |
|---|---|---|
| EP | 0 882 983 A2 | 12/1998 |
| EP | 2 202 516 A | 6/2010 |
| JP | 07-294518 A | 11/1995 |
| JP | 2002-207034 A | 7/2002 |
| JP | 4248017 B2 | 4/2009 |

OTHER PUBLICATIONS

Communication dated Jul. 1, 2020, issued in Brazilian Application No. BR112013027349-6.
Communication dated Feb. 5, 2020 in Indian Application No. 3335/KOLNP/2013.

*Primary Examiner* — Adam Weidner
*Assistant Examiner* — Tiffany M Gough
(74) *Attorney, Agent, or Firm* — Sughrue Mion, PLLC

(57) ABSTRACT

The present invention provides a method for classifying and counting leukocytes which allows classification and count of normal leukocytes as well as discrimination between blast cells and atypical lymphocytes. The present invention also provides a regent kit and reagent for classifying leukocyte which are used for classifying and counting leukocytes in biological samples.

7 Claims, 9 Drawing Sheets

| 2nd reagent B (Phthalate 20 mM, pH 7.0) |  Centroid distance 62.9 |
| --- | --- |
| 2nd reagent G (Phthalate 20 mM, pH 6.0) |  Centroid distance 69.7 |
| 2nd reagent O (Phthalate 40 mM, pH 6.0) |  Centroid distance 80.6 |

FIG. 3

| 2nd reagent | Measurement of abnormal specimen 2 |
|---|---|
| 2nd reagent B (Phthalate 20 mM, pH 7.0) | Centroid distance 40.2 |
| 2nd reagent I (Phthalate 30 mM, pH 7.0) | Centroid distance 47.7 — Monocytes |
| 2nd reagent K (Phthalate 30 mM, pH 6.0) | Centroid distance 46.0 — Monocytes |
| 2nd reagent O (Phthalate 40 mM, pH 6.0) | Centroid distance 48.4 — Monocytes |

FIG. 4A

| 2nd reagent | Measurement of abnormal specimen 3 |
|---|---|
| 2nd reagent B (Phthalate 20 mM, pH 7.0) | Centroid distance 52.4 |
| 2nd reagent I (Phthalate 30 mM, pH 7.0) | Centroid distance 59.4 — Monocytes + Myeloblasts |
| 2nd reagent K (Phthalate 30 mM, pH 6.0) | Centroid distance 58.0 — Monocytes + Myeloblasts |

METHOD FOR CLASSIFYING/COUNTING LEUKOCYTES, REAGENT KIT FOR CLASSIFYING LEUKOCYTES, AND REAGENT FOR CLASSIFYING LEUKOCYTES

CROSS-REFERENCE TO RELATED APPLICATION

This application is a divisional of U.S. application Ser. No. 14/061,333 filed Oct. 23, 2013, which is a continuation of International Application PCT/JP2012/060432 filed Apr. 18, 2012, which claims benefit of Japanese patent application JP 2011-101595 filed Apr. 28, 2011, the contents of all of which are incorporated herein by reference in their entireties.

BACKGROUND OF THE INVENTION

The present invention relates to a method for classifying and counting leukocytes in biological samples. The present invention also relates to a regent kit and reagent for classifying leukocyte which are used for classifying and counting leukocytes in biological samples.

Normal leukocytes are generally classified into five types: lymphocytes, monocytes, neutrophils, eosinophils and basophils. Normal peripheral blood contains these blood cells at certain proportions. However, a subject with a disease may have an increased or decreased number of certain blood cells. Therefore, in the field of clinical tests, classification and count of leukocytes may provide very useful information for diagnoses of diseases.

Diseases such as hematopoietic malignancies and virus infections cause occurrence of cells which are not present in normal peripheral blood. For example, in acute leukemia, immature leukocytes, i.e. "blast cells (myeloblasts, lymphoblasts)" occur in peripheral blood. On the other hand, in virus infections or drug allergies, lymphocytes activated by antigen stimulation, i.e. "atypical lymphocytes" occur in peripheral blood. It is very important to detect atypical lymphocytes and blast cells from peripheral blood by differentiating therebetween in order to screen or diagnose diseases.

In recent years, various automated blood cell counters are commercially available to which the principle of flow cytometry has been applied. These counters allow automated classification and count of blood cells in samples. Blood cell classifying reagents for measurements on automated blood cell counters are also commercially available. Upon measurements of specimens on automated blood cell counters using these reagents, signals of respective blood cells appear in certain regions on scattergrams.

A number of such blood cell classifying reagents is known in the art. For example, Japanese Patent No. 4248017 discloses a method that allows classification and count of both abnormal and normal leukocytes. In this method, a reagent kit is used which is a combination of a staining solution for specifically staining RNA and a hemolytic agent containing cationic and nonionic surfactants. Meanwhile, U.S. Patent Application No. 2009/0023129 discloses a method for classifying and counting normal leukocytes and detecting abnormal leukocytes. In this method, a reagent is used which comprises a staining solution containing a certain fluorescent dye and a hemolytic agent containing cationic and nonionic surfactants.

BRIEF SUMMARY OF THE INVENTION

As described above, specimens obtained from subjects may contain, in addition to normal leukocytes, abnormal leukocytes such as blast cells and atypical lymphocytes.

However, in methods using the reagents disclosed in Japanese Patent No. 4248017 and U.S. Patent Application No. 2009/0023129, signals of abnormal leukocytes, i.e. blast cells and atypical lymphocytes, may appear in similar regions on scattergrams, and thus it is difficult to detect blast cells and atypical lymphocytes by differentiating therebetween.

Thus the present invention is to provide a method for classifying and counting leukocytes that allows classification and count of normal leukocytes and detection of blast cells and atypical lymphocytes by differentiating therebetween. The present invention is also to provide a reagent kit for classifying leukocytes and a reagent for classifying leukocytes that allow classification and count of normal leukocytes and detection of blast cells and atypical lymphocytes by differentiating therebetween.

In measurements on flow cytometers using conventional leukocyte classification reagents, signals of blast cells and atypical lymphocytes on scattergrams appear in the vicinity of or in the overlapping region of the regions where signals of normal lymphocytes and normal monocytes are present. The present inventors hypothesized that by separating the region where the signal of normal lymphocytes appears from the region where the signal of normal monocytes appears, the signal of abnormal leukocytes can be separated from the signal of normal leukocytes and the sensitivity for detection of abnormal leukocytes can be improved.

Therefore, the present inventors investigated for a method for classifying leukocytes which makes it possible to separate the region where the signal of normal lymphocytes appears from the region where the signal of normal monocytes appears. As a result, the present inventors have surprisingly found that certain combinations of the concentration of an aromatic organic acid and pH in the reagent can improve the detection accuracy of abnormal leukocytes and allow detection of blast cells and atypical lymphocytes by differentiating therebetween, thereby achieving the present invention.

Thus the present invention provides a method for classifying and counting leukocytes comprising the steps of:

preparing a measurement sample by mixing a biological sample; a first reagent containing a fluorescent dye capable of staining nucleic acid; and a second reagent containing cationic and nonionic surfactants for lysing erythrocytes and damaging cell membranes of leukocytes so as to be permeable to the fluorescent dye and an aromatic organic acid at a concentration of not less than 20 mM and not more than 50 mM;

applying light to the prepared measurement sample and obtaining scattered light information and fluorescence information generated thereby; and based on the obtained scattered light information and fluorescence information, classifying the leukocytes in the biological sample and detecting blast cells and atypical lymphocytes by differentiating therebetween;

wherein when the second reagent contains the aromatic organic acid at a concentration of not less than 20 mM and less than 30 mM, the second reagent has pH of not lower than 5.5 and not higher than 6.4, and when the second reagent contains the aromatic organic acid at a concentration of not less than 30 mM and not more than 50 mM, the second reagent has pH of not lower than 5.5 and not higher than 7.0.

The present invention also provides a reagent kit for classifying leukocytes comprising a first reagent containing a fluorescent dye capable of staining nucleic acid and a second reagent containing cationic and nonionic surfactants for lysing erythrocytes and damaging cell membranes of leukocytes so as to be permeable to the fluorescent dye and an aromatic organic acid at a concentration of not less than 20 mM and not more than 50 mM, wherein when the second reagent contains the aromatic organic acid at a concentration of not less than 20 mM and less than 30 mM, the second reagent has pH of not lower than 5.5 and not higher than 6.4, and when the second reagent contains the aromatic organic acid at a concentration of not less than 30 mM and not more than 50 mM, the second reagent has pH of not lower than 5.5 and not higher than 7.0.

The present invention further provides a reagent for classifying leukocytes comprising a fluorescent dye capable of staining nucleic acid, a cationic surfactant, a nonionic surfactant and an aromatic organic acid, wherein the reagent contains the aromatic organic acid at a concentration of not less than 20 mM and not more than 50 mM, and wherein when the reagent contains the aromatic organic acid at a concentration of not less than 20 mM and less than 30 mM, the reagent has pH of not lower than 5.5 and not higher than 6.4, and when the reagent contains the aromatic organic acid at a concentration of not less than 30 mM and not more than 50 mM, the reagent has pH of not lower than 5.5 and not higher than 7.0.

The method for classifying and counting leukocytes, the reagent kit for classifying leukocytes and the reagent for classifying leukocytes according to the present invention allow classification and count of normal leukocytes as well as detection of blast cells and atypical lymphocytes by differentiating therebetween.

BRIEF DESCRIPTION OF THE DRAWINGS

FIG. 3 shows scattergrams obtained by measurements of a blood specimen containing abnormal leukocytes using the reagents in Example 3;

FIG. 4A and FIG. 4B show scattergrams obtained by measurements of a blood specimen containing abnormal leukocytes using the reagents in Example 3;

DETAILED DESCRIPTION OF THE INVENTION

Figure 1:
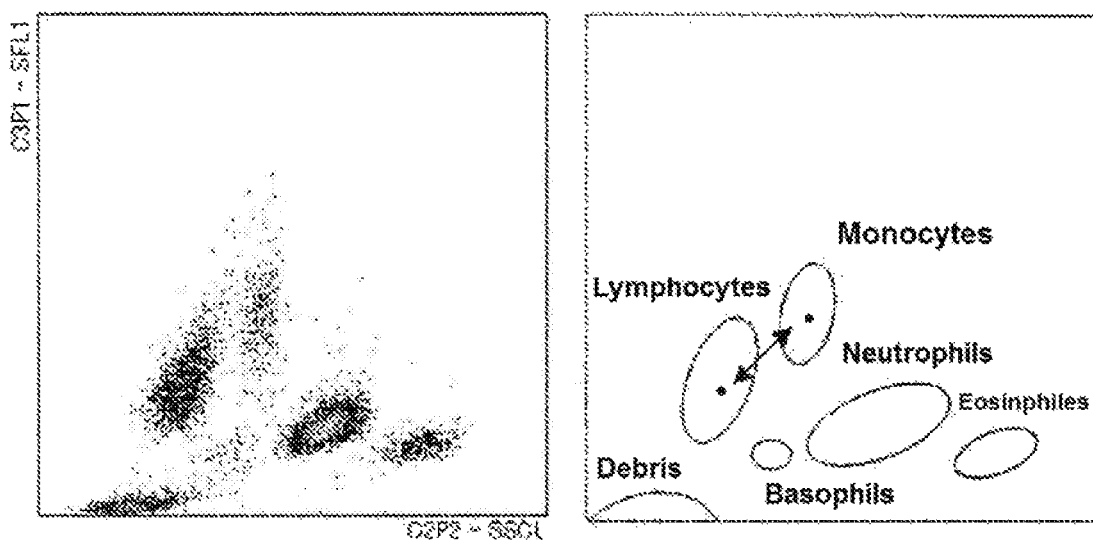
FIG. 1 shows a scattergram and a diagram obtained by a measurement of a normal blood specimen using the reagent kit for classifying leukocytes of the present invention.

In the embodiments of the present invention, the biological sample is not particularly limited as far as it is a body fluid sample containing leukocytes. The biological sample may include, for example, blood, bone marrow fluid, urine, samples obtained by apheresis and the like obtained from mammals, preferably from humans. The biological sample may be a sample possibly containing abnormal leukocytes. The leukocyte as used herein comprises a normal leukocyte and an abnormal leukocyte. Normal leukocytes are generally classified into four types: lymphocytes, monocytes, eosinophils and granulocytes other than eosinophils, or five types: lymphocytes, monocytes, neutrophils, eosinophils and basophils.

As used herein abnormal leukocytes means leukocytes which are normally not present in peripheral blood. The abnormal leukocytes may include, for example, atypical lymphocytes and blast cells. The atypical lymphocytes are lymphocytes which are activated by antigen stimulation and have been morphologically modified by responding to the stimulation. Atypical lymphocytes occur in peripheral blood of patients with diseases such as virus infections, drug allergies and the like. The blast cells refer to immature leukocytes such as myeloblasts, lymphoblasts and the like. Myeloblasts occur in peripheral blood of patients with acute myeloid leukemia and lymphoblasts occur in peripheral blood of patients with acute lymphocytic leukemia.

The reagent kit for classifying leukocytes is hereinafter described which is used in the method for classifying and counting leukocytes of the present invention.

The reagent kit for classifying leukocytes of the present invention (hereinafter also referred to as "reagent kit") comprises a first reagent and a second reagent. These reagents in the reagent kit are hereinafter described.

[First Reagent]

The first reagent contained in the reagent kit of the present invention comprises a fluorescent dye capable of staining nucleic acid. In the embodiments of the present invention, the first reagent is a reagent for fluorescent staining nucleic acid of nucleated cells in a biological sample treated with the second reagent described hereinbelow. Treatment of a biological sample with the first reagent allows staining of blood cells having nucleic acid such as normal leukocytes and abnormal leukocytes.

In the embodiments of the present invention, the fluorescent dye is not particularly limited as far as it can stain nucleic acid and can be appropriately selected depending on the wavelength of light emitted from a light source. The fluorescent dye may include, for example, propidium iodide, ethidium bromide, ethidium-acridine heterodimer, ethidium diazide, ethidium homodimer-1, ethidium homodimer-2, ethidium monoazide, trimethylenebis[[3-[[4-[[(3-methylbenzothiazol-3-ium)-2-yl]methylene]-1,4-di hydroquinolin]-1-yl]propyl]dimethylaminium] tetraiodide (TOTO-1), 4-[(3-methylbenzothiazol-2(3H)-yliden)methyl]-1-[3-(trimethylaminio)propyl]quinolinium diiodide (TO-PRO-1), N,N,N',N'-tetramethyl-N,N'-bis[3-[4-[3-[(3-methylbenzothiazol-3-ium)-2-yl]-2-propyliden]-1,4-dihydroquinolin-1-yl]propyl]-1,3-propanediaminium tetraiodide (TOTO-3), 2-[3-[[1-[3-(trimethylaminio)propyl]-1,4-dihydroquinolin]-4-yliden]-1-propenyl]-3-methylbenzothiazol-3-ium diiodide (TO-PRO-3) and fluorescent dyes represented by the following general formula I). Among these, the fluorescent dyes represented by the following general formula (I) are preferable.

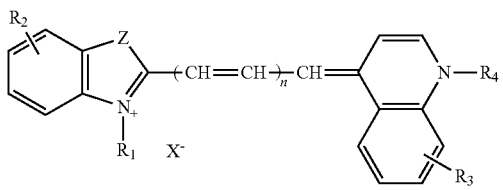
(I)

In the formula I), $R_1$ and $R_4$ are the same or different from each other and respectively are a hydrogen atom, an alkyl group, an alkyl chain having a hydroxyl group, an alkyl chain having an ether group, an alkyl chain having an ester group or a benzyl group that may have a substituent; $R_2$ and $R_3$ are the same or different from each other and respectively are a hydrogen atom, a hydroxyl group, a halogen, an alkyl group, an alkenyl group, an alkynyl group, an alkoxy group, an alkylsulphonyl group or a phenyl group; Z is a sulphur atom, an oxygen atom or a carbon atom having a methyl group; n is 0, 1, 2 or 3; and $X^-$ is an anion.

In the embodiments of the present invention, the alkyl group may be linear or branched. In the embodiments of the present invention, it is preferable that in the formula (I), when one of $R_1$ and $R_4$ is an alkyl group having 6 to 18 carbon atoms, the other is a hydrogen atom or an alkyl group having less than 6 carbon atoms. Among the alkyl groups having 6 to 18 carbon atoms, the alkyl group having 6, 8 or 10 carbon atoms is preferable.

In the embodiments of the present invention, the substituent of the benzyl group in $R_1$ and $R_4$ in the formula I) may include, for example, alkyl groups having 1 to 20 carbon atoms, alkenyl groups having 2 to 20 carbon atoms and alkynyl groups having 2 to 20 carbon atoms. Among these, a methyl or ethyl group is particularly preferable.

In the embodiments of the present invention, the alkenyl group in $R_2$ and $R_3$ in the formula (I) may include, for example, alkenyl groups having 2 to 20 carbon atoms. The alkoxy group in $R_2$ and $R_3$ may include alkoxy groups having 1 to 20 carbon atoms. Among these, a methoxy or ethoxy group is particularly preferable.

In the embodiments of the present invention, the anion $X^-$ in the formula (I) may include halogen ions such as $F^-$, $Cl^-$, $Br^-$ and $I^-$, $CF_3SO_3^-$, $BF_4^-$ and the like.

In the embodiments of the present invention, the first reagent may contain one or two or more fluorescent dyes.

In the embodiments of the present invention, the concentration of the fluorescent dye in the first reagent may vary depending on the type of the fluorescent dye and is usually 0.01 to 100 pg/µL, preferably 0.1 to 10 pg/µL. When the fluorescent dye in the first reagent is, for example, the fluorescent dye represented by the formula (I), the first reagent preferably contain the fluorescent dye at a concentration of 0.2 to 0.6 pg/µL, more preferably 0.3 to 0.5 pg/µL.

In the embodiments of the present invention, the first reagent can be obtained by dissolving the fluorescent dye in a suitable solvent so as to obtain the concentration described above. The solvent is not particularly limited as far as it can dissolve the fluorescent dye and may include, for example, water, organic solvents and mixtures thereof.

The organic solvents may include, for example, alcohols, ethylene glycol, dimethyl sulphoxide (DMSO) and the like. The fluorescent dye is preferably dissolved in an organic solvent because the dye may have a decreased storage stability in aqueous solutions.

In the embodiments of the present invention, the first reagent may be a commercial staining reagent for leukocyte measurements. Such a staining reagent may include, for example, Stromatolyzer 4DS (Sysmex Corporation). Stromatolyzer 4DS is a staining reagent containing the fluorescent dye represented by the formula (I).

[Second Reagent]

The second reagent contained in the reagent kit of the present invention comprises surfactants, i.e. cationic and nonionic surfactants, for lysing erythrocytes and damaging cell membranes of leukocytes so as to be permeable to the fluorescent dye. The second reagent further comprises an aromatic organic acid at a concentration of not less than 20 mM and not more than 50 mM.

In the embodiments of the present invention, when the second reagent contains the aromatic organic acid at a concentration of not less than 20 mM and less than 30 mM, the second reagent has pH of not lower than 5.5 and not higher than 6.4, more preferably not lower than 5.5 and not higher than 6.2. When the second reagent contains the aromatic organic acid at a concentration of not less than 30 mM and not more than 50 mM, preferably not less than 40 mM and not more than 50 mM, the second reagent has pH of not lower than 5.5 and not higher than 7.0. Still more preferably, when the second reagent contains the aromatic organic acid at a concentration of not less than 40 mM and not more than 50 mM, the second reagent has pH of not lower than 5.5 and not higher than 6.2.

In the embodiments of the present invention, treatment with the second reagent of a biological sample allows lysis of erythrocytes in the biological sample and damages cell membranes of leukocytes so as to be permeable to the fluorescent dye. When the biological sample contains abnormal leukocytes, the second reagent can also damage cell membranes of the abnormal leukocytes so as to be permeable to the fluorescent dye.

The blood cells damaged on cell membranes by the second reagent are stained with the fluorescent dye in the first reagent. When the second reagent has the concentration of the aromatic organic acid and pH within the above ranges, the region where the signal of normal lymphocytes appears and the region where the signal of normal monocytes appears detected by flow cytometers and the like can be separated to such extent that the detection accuracy of abnormal leukocytes is improved and differentiation of blast cells from atypical lymphocytes is possible.

As used herein, the aromatic organic acid means an acid having at least one aromatic ring in a molecule or a salt thereof. The aromatic organic acid may include, for example, aromatic carboxylic acids, aromatic sulphonic acids and the like. In the embodiments of the present invention, the aromatic organic acid which is suitably used is phthalic acid, benzoic acid, salicylic acid, hippuric acid, p-aminobenzenesulphonic acid, benzenesulphonic acid and salts thereof. The second reagent may contain one or two or more aromatic organic acids. When the second reagent contains two or more aromatic organic acids, the second reagent may contain the aromatic organic acids at a total concentration thereof of not less than 20 mM and not more than 50 mM.

In the embodiments of the present invention, the cationic surfactant may be a quaternary ammonium salt surfactant or a pyridinium salt surfactant. The quaternary ammonium salt surfactant may include, for example, surfactants represented by the following formula (II) having 9 to 30 carbon atoms in total:

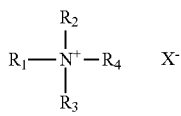 (II)

In the formula (II), $R_1$ is an alkyl or alkenyl group having 6 to 18 carbon atoms; $R_2$ and $R_3$ are the same or different from each other and are respectively an alkyl or alkenyl group having 1 to 4 carbon atoms; $R_4$ is an alkyl or alkenyl group having 1 to 4 carbon atoms or a benzyl group; and $X^-$ is a halogen ion.

In the formula II), $R_1$ is preferably an alkyl or alkenyl group having 6, 8, 10, 12 or 14 carbon atoms and is particularly preferably a linear alkyl group. More specifically, $R_1$ may include octyl, decyl and dodecyl groups. $R_2$ and $R_3$ are preferably a methyl, ethyl or propyl group. $R_4$ is preferably a methyl, ethyl or propyl group.

The pyridinium salt surfactant may include, for example, surfactants represented by the following formula (III).

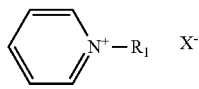 (III)

In the formula (III), $R_1$ is an alkyl or alkenyl group having 6 to 18 carbon atoms; and $X^-$ is a halogen ion.

In the formula (III), $R_1$ is preferably an alkyl or alkenyl group having 6, 8, 10, 12 or 14 carbon atoms and is particularly preferably a linear alkyl group. More specifically, $R_1$ may include octyl, decyl and dodecyl groups.

In the embodiments of the present invention, the concentration of the cationic surfactant in the second reagent may be appropriately adjusted depending on the type of the surfactant and is usually 10 to 10,000 ppm, preferably 100 to 1,000 ppm.

In the embodiments of the present invention, the nonionic surfactant is preferably a polyoxyethylene nonionic surfactant represented by the following formula (VI).

$$R_1-R_2-(CH_2CH_2O)_n-H \quad (VI)$$

In the formula (VI), $R_1$ is an alkyl, alkenyl or alkynyl group having 8 to 25 carbon atoms; $R_2$ is an oxygen atom, —COO— or

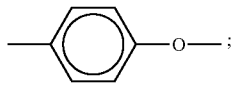

and
n is an integer of 10 to 50.

Specific examples of the nonionic surfactant may include polyoxyethylene alkyl ethers, polyoxyethylene sterols, polyoxyethylene castor oils, polyoxyethylene sorbitan fatty acid esters, polyoxyethylene alkylamines, polyoxyethylene polyoxypropylene alkyl ethers and the like.

In the embodiments of the present invention, the second reagent may usually contain the nonionic surfactant at a concentration of 10 to 100,000 ppm, preferably 100 to 10,000 ppm, more preferably 1,000 to 5,000 ppm.

In the embodiments of the present invention, the second reagent may contain a buffering agent in order to maintain a constant pH. The buffering agent may include, for example, citrate salts, HEPES, phosphate salts and the like. The aromatic organic acid may exhibit a buffering effect in some cases. When such an aromatic organic acid is used, a buffering agent may be optionally added to the second reagent.

In the embodiments of the present invention, the second reagent preferably have the osmotic pressure of, without limitation, 20 to 150 mOsm/kg in order to effectively lyse erythrocytes.

In the embodiments of the present invention, the second reagent can be obtained by dissolving the surfactants, the aromatic organic acid or a salt thereof and optionally the buffering agent to a suitable solvent so as to obtain the concentration of the aromatic organic acid described above and adjusting pH thereof with NaOH, HCl and the like.

The solvent is not particularly limited as far as it can dissolve the above components and may include, for example, water, organic solvents and mixtures thereof. The organic solvents may include, for example, alcohols, ethylene glycol, DMSO and the like.

The reagent kit described hereinabove contains a distinct first reagent and second reagent. However, the present invention is not limited to this embodiment and may encompass a reagent having the compositions of the first reagent and the second reagent without particular limitation.

[Method for Classifying and Counting Leukocytes]

By using the reagent kit for classifying leukocytes or the reagent, leukocytes in biological samples can be classified and counted. The method for classifying and counting leukocytes using the reagent kit of the present invention (hereinafter simply referred to as the "method") is hereinafter described.

In the method of the present invention, a measurement sample is prepared by mixing a biological sample, the first reagent and the second reagent in the reagent kit in order to lyse erythrocytes in the biological sample and stain nucleic acid of leukocytes (preparation step).

In the embodiments of the present invention, the biological sample and the first reagent or the second reagent are mixed at a volume ratio of the biological sample:the first or second reagent of 1:1 to 1:1,000, more preferably 1:10 to 1:100. The ratio of the mixture of the first and second reagents to the biological sample is such that the volume ratio of the biological sample:the mixture is 1:5 to 1:1,000, more preferably 1:10 to 1:100. Mixing the biological sample and the first and second reagents at the above ratio allows prompt lysis of erythrocytes and staining of nucleic acid of leukocytes. When the biological sample contains abnormal leukocytes, nucleic acid of the abnormal leukocytes is also stained. A sufficient amount of the biological sample used for the measurement is about 5 to 500 μL.

In the preparation step, the biological sample, the first reagent and the second reagent may be mixed in any order without limitation. For example, the first reagent and the second reagent may be mixed and then the obtained mixture may be mixed with the biological sample. Alternatively, the second reagent may be mixed with the biological sample and then the obtained mixture may be mixed with the first reagent. In the embodiments of the present invention, mixing by any order can provide similar results.

In the embodiments of the present invention, it is preferable that the biological sample, the first reagent and the second reagent are mixed prior to incubation at a temperature of 15 to 50° C., preferably 30 to 45° C. for 5 to 120 seconds, preferably 5 to 30 seconds.

In the method of the present invention, light is applied to the measurement sample prepared in the previous step to obtain scattered light information and fluorescence information (measurement step).

In the embodiments of the present invention, the measurement step is preferably carried out on a flow cytometer. In measurements using a flow cytometer, light is applied to stained leukocytes when they pass through a flow cell of the flow cytometer, so that scattered light information and fluorescence information can be obtained as signals generated from the leukocytes.

In the embodiments of the present invention, the scattered light information is not particularly limited as far as it is scattered light that can be measured on conventional commercially available flow cytometers. The scattered light information may include, for example, a pulse width and an intensity of scattered light such as forward scattered light (e.g. light receiving angle of about 0 to 20 degrees), side scattered light (light receiving angle of about 90 degrees) and the like.

It is known in the art that side scattered light reflects internal information of cells such as nuclei and granules and forward scattered light reflects information on the size of cells. In the embodiments of the present invention, the scattered light information is preferably a side scattered light intensity.

The fluorescence information is information obtained by applying excitation light having an appropriate wavelength to the stained leukocytes and measuring excited fluorescence. The fluorescence is emitted from nucleic acid and the like in the cells stained with the fluorescent dye in the first reagent. The receiving wavelength can be appropriately selected depending on the fluorescent dye in the first reagent.

In the embodiments of the present invention, the light source of a flow cytometer is not particularly limited and may be a light source having a suitable wavelength for excitation of the fluorescent dye. The light source may be, for example, a red semiconductor laser, a blue semiconductor laser, an argon laser, a He—Ne laser, a mercury arc lamp and the like. The semiconductor lasers are particularly suitable because of their inexpensiveness compared to gas lasers.

In the method of the present invention, leukocytes in the biological sample is classified and counted based on the scattered light information and the fluorescence information (classification and count step).

In the embodiments of the present invention, leukocytes are preferably classified and counted by preparing a scattergram having two axes of side scattered light information and fluorescence information and analyzing the obtained scattergram on an appropriate analysis software. For example, when a scattergram is generated having a side scattered light intensity on the X-axis and a fluorescent intensity on the Y-axis, as shown in the right panel in FIG. 1, leukocytes are classified into 5 groups (clusters) of lymphocytes, monocytes, neutrophils, eosinophils and basophils. An analysis software then provides windows which enclose the respective groups on the scattergram and allows count of the number of cells therein.

In FIG. 1, leukocytes are classified into 5 clusters. However, the present invention is not limited to this embodiment and, for example, neutrophils and basophils may be classified as one cluster to classify leukocytes into 4 clusters.

In the embodiments of the present invention, the biological sample may be a sample possibly containing abnormal leukocytes. As described above, the reagent kit of the present invention allows separation of the region where the signal of normal lymphocytes appears and the region where the signal of normal monocytes appears on scattergrams detected on a flow cytometer. Thus the method of the present invention allows detection of blast cells and atypical lymphocytes by differentiating therebetween among abnormal leukocytes contained in a biological sample in the step of classifying and counting leukocytes. Blast cells and atypical lymphocytes may be differentiated by, for example, preliminarily defining on scattergrams the region where the signal of blast cells appears and the region where the signal of atypical lymphocytes appears. For example, when a signal is detected in the preliminarily defined region where the signal of blast cells appears, it is determined that the biological sample contains blast cells, and when a signal is detected in the preliminarily defined region where the signal of atypical lymphocytes appears, it is determined that the biological sample contains atypical lymphocytes, thus allowing detection of blast cells and atypical lymphocytes.

In the embodiments of the present invention, blast cells may include, for example, myeloblasts.

The present invention is further described in detail hereinafter by way of examples which do not limit the present invention.

EXAMPLES

Example 1

In the present Example, the concentration of the aromatic organic acid in the second reagent and pH of the second reagent are studied in order to discriminate the position where the signal of normal lymphocytes appears from the position where the signal of normal monocytes appears on scattergrams.

The first reagent used was Stromatolyzer 4DS (Sysmex Corporation). The second reagent was prepared by mixing dodecyltrimethylammonium chloride (LTAC: Tokyo Chemical Industry Co., Ltd.), polyoxyethylene (30) cetyl ether (BC30TX: Nikko Chemicals Co., Ltd.), potassium hydrogen phthalate (hereinafter referred to as phthalate: Wako Pure Chemical Industries, Ltd.) and EDTA-2K (Chubu Chelest K.K.) according to the compositions shown in the following Table 1. pH was adjusted with a NaOH solution.

LTAC is a cationic surfactant, BC30TX is a nonionic surfactant and the phthalate is an aromatic organic acid.

TABLE 1

| Name of regaent | LTAC (ppm) | BC30TX (ppm) | Phthalate (mM) | EDTA-2K (g/dL) | HEPES (mM) | pH |
| --- | --- | --- | --- | --- | --- | --- |
| 2nd reagent A | 685 | 1850 | 20 | 0.2 | 10 | 7.2 |
| 2nd reagent B | 685 | 1850 | 20 | 0.2 | 10 | 7.0 |
| 2nd reagent C | 685 | 1750 | 20 | 0 2 | — | 7.0 |
| 2nd reagent D | 685 | 1750 | 20 | 0.2 | — | 6.8 |
| 2nd reagent E | 685 | 1750 | 20 | 0.2 | — | 6.4 |
| 2nd reagent F | 685 | 1750 | 20 | 0.2 | — | 6.2 |
| 2nd reagent G | 685 | 1750 | 20 | 0.2 | — | 6.0 |
| 2nd reagent H | 685 | 1750 | 20 | 0.2 | — | 5.5 |
| 2nd reagent I | 685 | 1750 | 30 | 0.2 | — | 7.0 |
| 2nd reagent J | 685 | 1750 | 30 | 0.2 | — | 6.8 |
| 2nd reagent K | 685 | 1750 | 30 | 0.2 | — | 6.0 |
| 2nd reagent L | 685 | 1750 | 30 | 0.2 | — | 5.5 |
| 2nd reagent M | 685 | 1750 | 40 | 0.2 | — | 7.0 |
| 2nd reagent N | 685 | 1750 | 40 | 0.2 | — | 6.8 |
| 2nd reagent O | 685 | 1750 | 40 | 0.2 | — | 6.0 |
| 2nd reagent P | 685 | 1750 | 40 | 0.2 | — | 5.5 |
| 2nd reagent Q | 685 | 1750 | 50 | 0.2 | — | 6.0 |

As shown in Table 1, only the second reagents A and B contain HEPES (Dojindo Laboratories) as a buffer. The second reagents A and B correspond to hemolytic agents of conventional leukocyte classifying reagents.

The biological samples used in the present Example are blood specimens (18 specimens) obtained from 18 healthy subjects. The specimens are respectively referred to as specimen Nos. 1 to 18.

A measurement sample was prepared by mixing 20 μL of a specimen, 20 μL of the first reagent and 1000 μL of the second reagent and incubating at 40° C. for 20 seconds. Measurement samples were prepared for specimen Nos. 1 to 10 with the second reagents A to D and G to Q and for specimen Nos. 11 to 18 with the second reagents B and E to G.

Light was applied to the measurement samples on a flow cytometer (hereinafter referred to as a FCM) and the side scattered light signal, the forward scattered light signal and the fluorescence signal generated from the cells in the samples were detected. The obtained signals were analyzed to measure normal leukocytes in the measurement samples. The FCM used had a light source of a red semiconductor laser having an excitation wavelength of 633 nm. The fluorescence signal detected was fluorescence having a wavelength of 600 nm or above (red fluorescence).

When a scattergram is prepared for each measurement sample having the side scattered light intensity on the X-axis and the fluorescence intensity on the Y-axis, leukocytes form clusters for different types of cells. These clusters are analyzed with an appropriate analysis software to identify the leukocyte clusters and calculate the number of cells in the respective leukocyte clusters, the proportion of the cells in the respective leukocyte clusters relative to the total number of cells and the position of the centroid of the respective leukocyte clusters. From the positions of the centroid of the respective leukocyte clusters, the distance between the centroids (hereinafter referred to as the centroid distance) is calculated.

As a reference to the centroid distance, FIG. 1 is provided. The left panel in FIG. 1 is a scattergram obtained by measuring a specimen from a healthy subject with the above first reagent and the second reagent O. The left panel in FIG. 1 shows that normal leukocytes in the specimen were classified into 5 types, i.e. lymphocytes, monocytes, neutrophils, eosinophils and basophils. In the right panel of FIG. 1, the respective blood cell clusters are identified and the centroids (•) for the clusters of lymphocytes and monocytes are indicated. The distance between two symbols (•) corresponds to the centroid distance.

The average centroid distance was 36.4 when 10 specimens (specimen Nos. 1 to 10) were measured with the second reagent A (phthalate concentration: 20 mM, pH 7.2). The average centroid distance was 38.3 when 18 specimens (specimen Nos. 1 to 18) were measured with the second reagent B (phthalate concentration: 20 mM, pH 7.0).

The average centroid distance obtained when 10 specimens (specimen Nos. 1 to 10) were measured with the second reagents C, D and H to Q, and the average centroid distance obtained when 18 specimens (specimen Nos. 1 to 18) were measure with the second reagent G and the average centroid distance obtained when 8 specimens (specimen Nos. 11 to 18) were measured with the second reagents E and F are shown in the following Table 2. The average centroid distances shown in Table 2 are classified according to the phthalate concentration and pH of the second reagent and shown in the following Table 3.

TABLE 2

| Name of reagent | Centroid distance |
| --- | --- |
| Second reagent C | 35.0 |
| Second reagent D | 35.5 |
| Second reagent E | 40.4 |
| Second reagent F | 42.9 |
| Second reagent G | 45.1 |
| Second reagent H | 45.4 |
| Second reagent I | 41.3 |
| Second reagent J | 40.5 |
| Second reagent K | 44.3 |
| Second reagent L | 45.8 |
| Second reagent M | 50.7 |
| Second reagent N | 47.7 |
| Second reagent O | 52.7 |
| Second reagent P | 48.0 |
| Second reagent Q | 52.3 |

TABLE 3

| pH | Phthalate concentration | | | |
| --- | --- | --- | --- | --- |
| | 20 mM | 30 mM | 40 mM | 50 mM |
| 7.0 | 35.0 | 41.3 | 50.7 | — |
| 6.8 | 35.5 | 40.5 | 47.7 | — |
| 6.4 | 40.4 | — | — | — |
| 6.2 | 42.9 | — | — | — |
| 6.0 | 45.2 | 44.3 | 52.7 | 52.3 |
| 5.5 | 45.4 | 45.8 | 48.0 | — |

From Table 3, it is found that when the second reagent has certain combinations of the phthalate concentration and pH, the region where the signal of monocytes appears is significantly discrete from the region where the signal of lymphocytes appears compared to the cases when the conventional second reagents A and B are used. Such combinations of the phthalate concentration and pH are: the phthalate concentration of not less than 20 mM and less than 30 mM and pH of not lower than 5.5 and not higher than 6.4; and the phthalate concentration of not less than 30 mM and not more than 50 mM and pH of not lower than 5.5 and not higher than 7.0.

Example 2

In the present Example, a blood specimen containing morphologically abnormal lymphocytes (hereinafter referred to as abnormal specimen 1) was measured with the first reagent and the second reagent B, G or O described in Example 1. The measurement by the FCM and calculation of the centroid distance were carried out in the same manner as Example 1.

Figure 2:
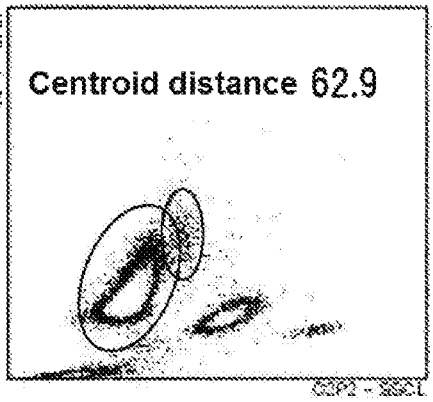
FIG. 2 shows scattergrams obtained by measurements of a blood specimen containing morphologically abnormal lymphocytes using the reagents in Example 2.
Figure 2:
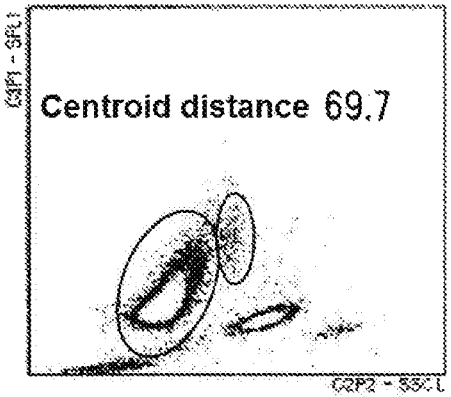
Figure 2:
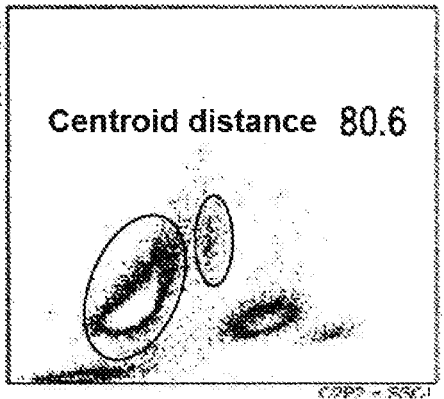

The scattergrams (X-axis: side scattered light intensity, Y-axis: fluorescence intensity) generated based on the measurements by the FCM using the reagents are shown in FIG. 2.

The centroid distance was 62.9 when the abnormal specimen 1 was measured with the second reagent B (phthalate concentration: 20 mM, pH 7.0). The centroid distance was 69.7 when the abnormal specimen 1 was measured with the second reagent G (phthalate concentration: 20 mM, pH 6.0). The centroid distance was 80.6 when the abnormal specimen 1 was measured with the second reagent O (phthalate concentration: 40 mM, pH 6.0).

The abnormal specimen 1 used in the present Example is a specimen which provides the signal of morphologically abnormal lymphocytes at a similar region as the signal of normal lymphocytes. Therefore the cluster of lymphocytes significantly expands on scattergrams. When the abnormal specimen 1 is measured with the second reagent B which is a conventional hemolytic agent, the cluster containing morphologically abnormal lymphocytes overlaps with the cluster of monocytes, and thus it is difficult to detect morphologically abnormal lymphocytes with accuracy.

On the other hand, measurements with the second reagent G or O of the reagent kit of the present invention allow the cluster of lymphocytes being significantly separated from the cluster of monocytes. Therefore even when abnormal specimens are measured as in the present Example, the cluster containing morphologically abnormal lymphocytes can be separated from the cluster of monocytes with accuracy. Accordingly morphologically abnormal lymphocytes can be detected with higher accuracy than conventional reagents.

Example 3

In the present Example, a biological sample containing morphologically abnormal lymphocytes (hereinafter referred to as abnormal specimen 2) and a biological sample containing myeloblasts (hereinafter referred to as abnormal specimen 3) were measured with the first reagent and the second reagent B, G, M or O described in Example 1.

The biological samples used in the present Example are two blood specimens which do not allow determination for abnormal leukocytes whether they are morphologically abnormal lymphocytes or myeloblasts in measurements using conventional reagents. This results from the fact that both signals of morphologically abnormal lymphocytes and of myeloblasts appear at about the same region on scattergrams. The measurement by the FCM and calculation of the centroid distance were carried out in the same manner as Example 1.

Figure 4B:
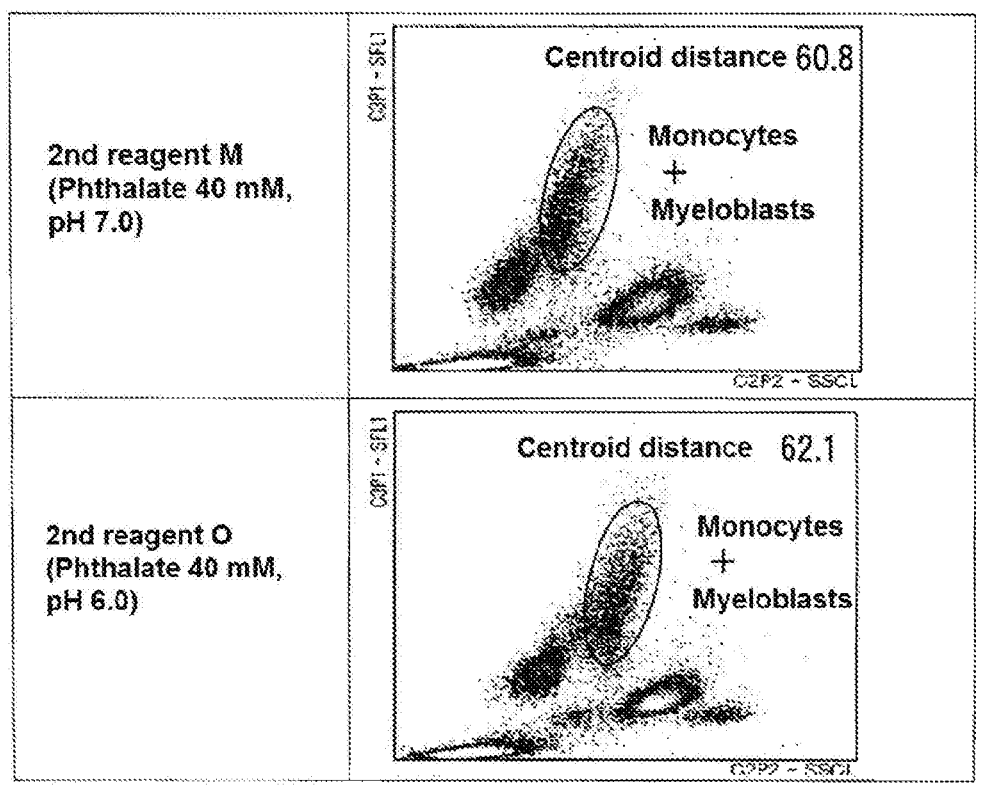

The scattergrams (X-axis: side scattered light intensity, Y-axis: fluorescence intensity) generated based on the measurements by the FCM using the reagents are shown in FIGS. 3, 4A and 4B.

From FIG. 3, it is found that when the abnormal specimen 2 is measured with the second reagent B which is a conventional reagent, the cluster of morphologically abnormal lymphocytes in the specimen appears from a region between the cluster of lymphocytes and the cluster of monocytes to a region above that region (towards the direction of higher fluorescence intensity). From FIG. 4A and FIG. 4B, it is also found that when the abnormal specimen 3 is measured with the second reagent B, the cluster of myeloblasts in the specimen also appears at a similar region as the cluster of morphologically abnormal lymphocytes contained in the abnormal specimen 2.

Namely, both clusters of abnormal leukocytes contained in the abnormal specimens 2 and 3 overlap partially with the clusters of lymphocytes and monocytes. The clusters of abnormal leukocytes in the abnormal specimens 2 and 3 also show similar features of distribution on scattergrams.

Thus the results of the measurements using the second reagent B which is a conventional reagent do not allow determination on which of morphologically abnormal lymphocytes and myeloblasts the specimens contain. Further the cluster of morphologically abnormal lymphocytes overlaps partially with the clusters of lymphocytes and monocytes, and thus it is difficult to classify and count normal lymphocytes and monocytes with accuracy.

From FIGS. 3, 4A and 4B, it is found that in the measurements using the second reagent I, K, M or O which is the second reagent of the reagent kit of the present invention, the cluster of lymphocytes and the cluster of monocytes appear separated on scattergrams. Accordingly, morphologically abnormal lymphocytes contained in the abnormal specimen 2 appear deviated towards the cluster of lymphocytes, resulting in accurate separation thereof from the cluster of monocytes. Moreover, myeloblasts contained in the abnormal specimen 3 appear deviated towards the cluster of monocytes, resulting in accurate separation thereof from the cluster of lymphocytes.

Thus the measurements with the second reagent of the reagent kit of the present invention allow apparent difference between the position where morphologically abnormal lymphocytes appear and the position where myeloblasts appear, and thus allow accurate determination on the type of abnormal leukocytes contained in specimens. Further, the measurements with the reagent of the present invention allow accurate discrimination of the cluster of abnormal leukocytes from the cluster of lymphocytes or the cluster of monocytes, and thus allow more accurate classification and count of normal monocytes or normal lymphocytes compared to the conventional reagents.

Example 4

In the present Example, biological samples containing morphologically abnormal lymphocytes were measured with the first reagent and the second reagent A or O described in Example 1. The morphologically abnormal lymphocytes contained in the biological sample in the present Example were confirmed to be atypical lymphocytes by morphological examinations.

The biological samples used in the present Example are two blood specimens (hereinafter respectively referred to as abnormal specimen 4 and abnormal specimen 5) which do not allow determination for abnormal leukocytes whether they are atypical lymphocytes or blast cells in measurements using conventional reagents. This results from, as described above, the fact that both signals of atypical lymphocytes and of blast cells appear at about the same region on scattergrams. The measurement by the FCM was carried out in the same manner as Example 1.

Figure 5A:
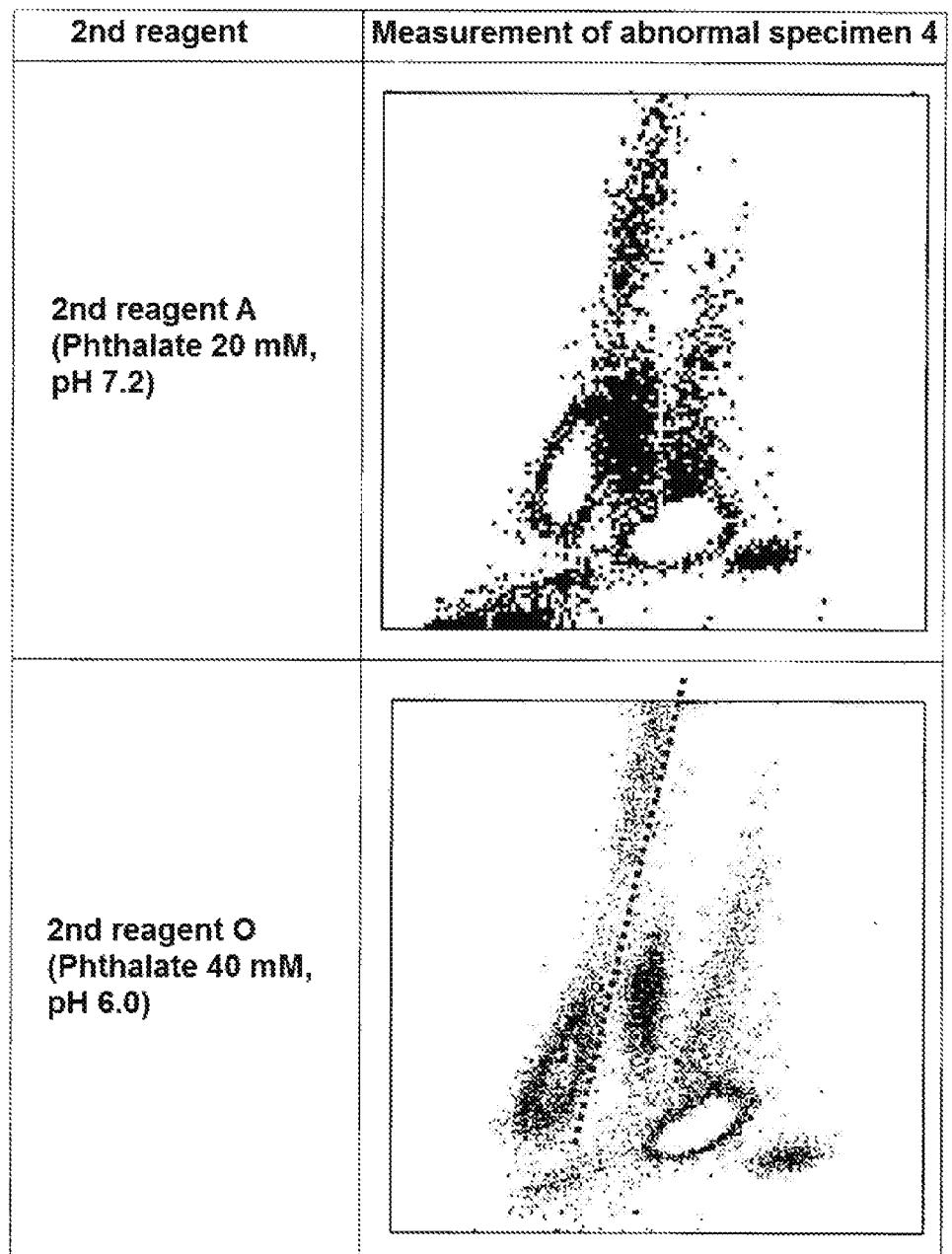
FIG. 5A and FIG. 5B show scattergrams obtained by measurements of a blood specimen containing abnormal leukocytes using the reagents in Example 4.
Figure 5B:
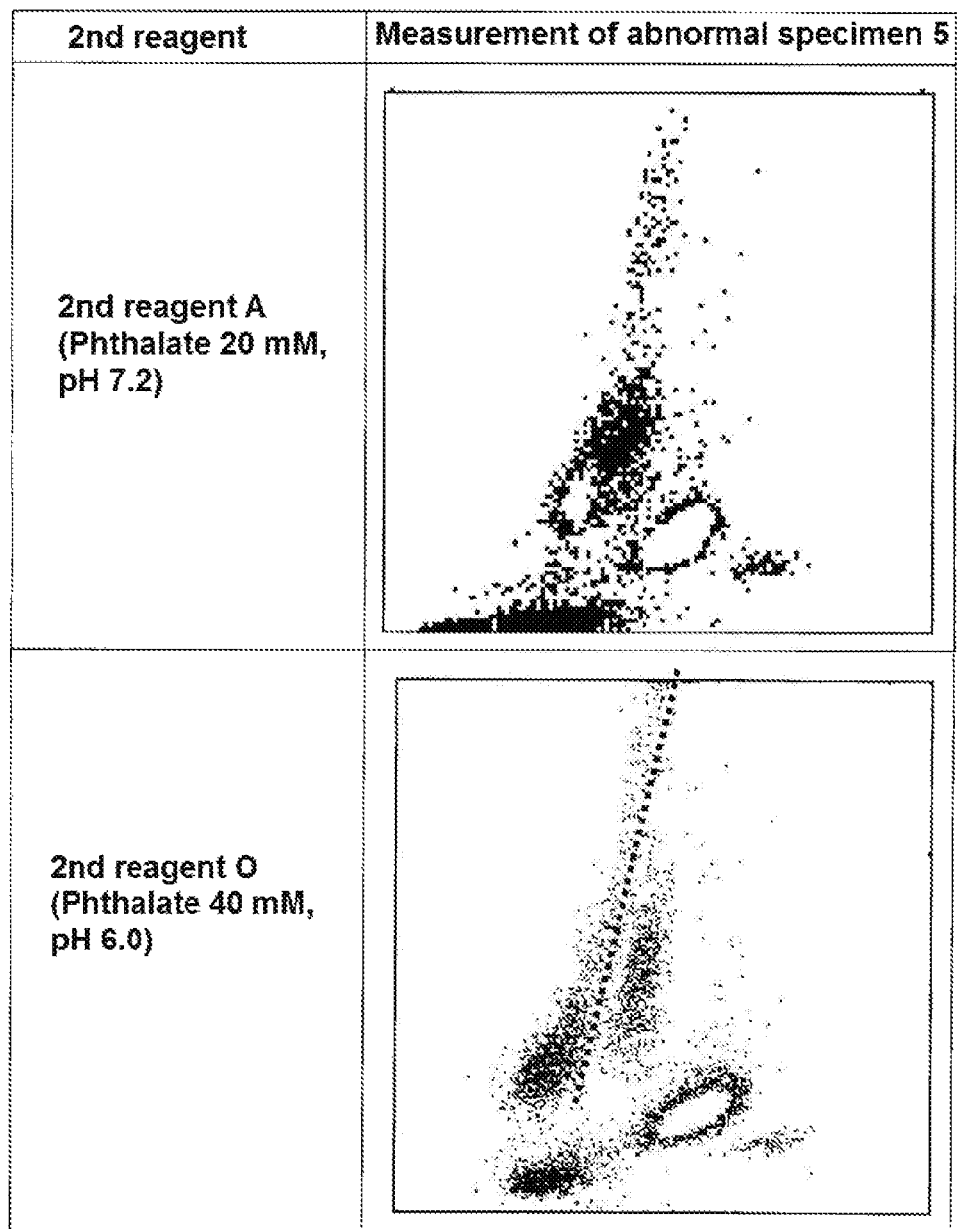

The scattergrams (X-axis: side scattered light intensity, Y-axis: fluorescence intensity) generated based on the measurements by the FCM using the reagents are shown in FIG. 5A and FIG. 5B. It is found that when the abnormal specimens 4 and 5 are measured with the second reagent A which is a conventional reagent, the cluster of atypical lymphocytes in the specimens appears from a region between the cluster of lymphocytes and the cluster of monocytes to a region above that region (towards the direction of higher fluorescence intensity). Because the cluster of blast cells also appears at almost similar region therewith (not shown), the cluster of atypical lymphocytes cannot be detected by differentiating thereof from the cluster of blast cells.

On the other hand, when the abnormal specimens 4 and 5 are measured with the second reagent 0, the cluster of monocytes was separated from the cluster of lymphocytes as well as the cluster of atypical lymphocytes appeared deviated towards the cluster of lymphocytes. As shown in FIG. 4A and FIG. 4B regarding Example 3, when abnormal specimens containing blast cells are measured with the second reagent o, blast cells appear deviated towards the cluster of monocytes. Accordingly, the cluster of atypical lymphocytes can be detected by differentiating thereof from the cluster of blast cells.

Example 5

In the present Example, a biological sample was measured with the first reagent and, as the second reagent, the second reagent A or G described in Example 1, or a second reagent R or S containing the phthalate and benzoic acid as the aromatic organic acid. The second reagents R and S were prepared by mixing LTAC, BC30TX, the phthalate, benzoic acid and EDTA-2K so as to obtain the compositions shown in the following Table 4.

TABLE 4

| Name of reagent | LTAC (ppm) | BC30TX (ppm) | Phthalate (mM) | Benzoic acid (mM) | EDTA-2K (g/dL) | pH |
|---|---|---|---|---|---|---|
| Second reagent R | 685 | 1850 | 20 | 20 | 0.2 | 6.0 |
| Second reagent S | 685 | 1850 | 20 | 30 | 0.2 | 6.0 |

The biological sample used in the present Example is a blood specimen obtained from a healthy subject. The measurement by the FCM and calculation of the centroid distance were carried out in the same manner as Example 1.

Figure 6A:
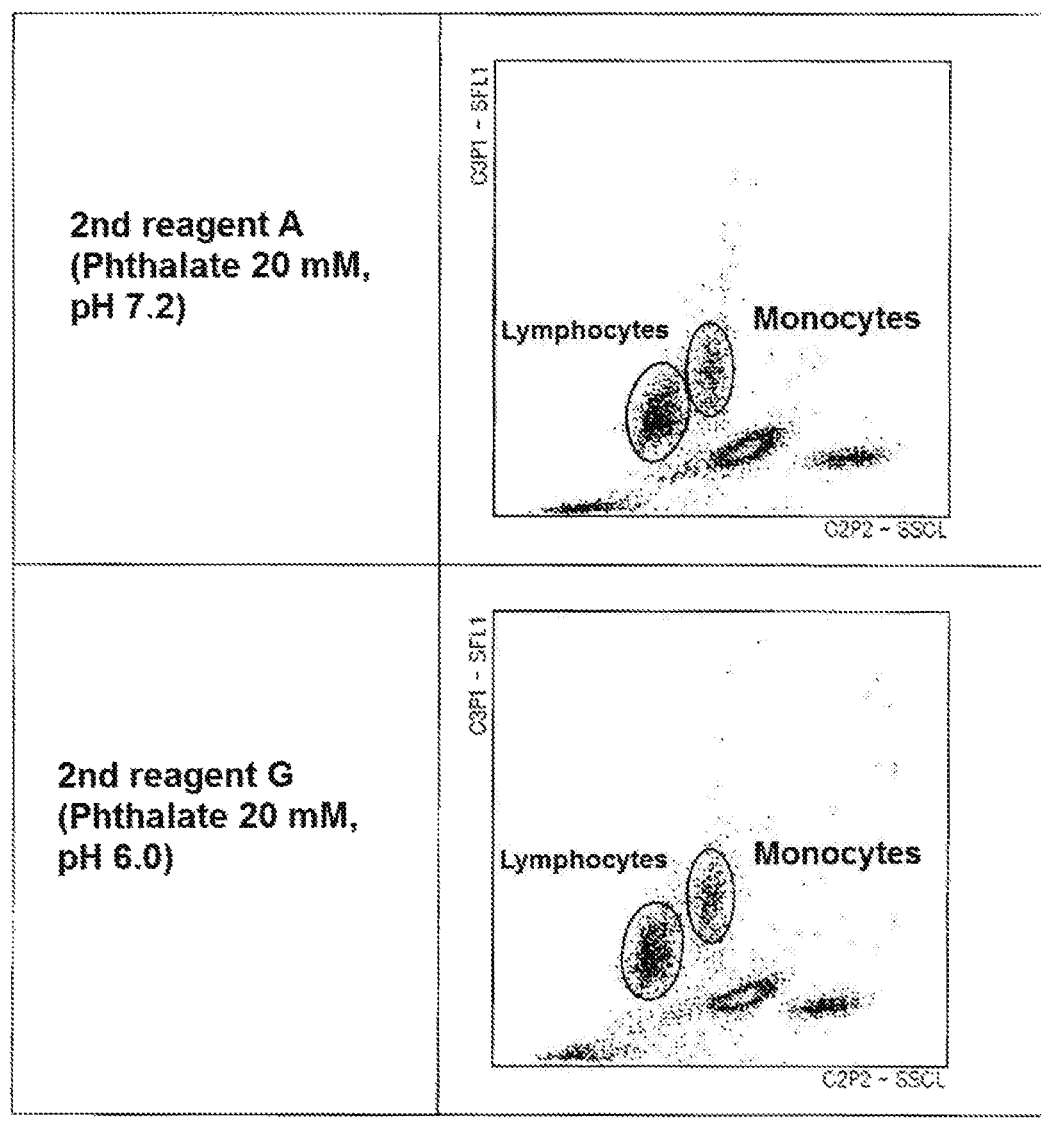
FIG. 6A and FIG. 6B show scattergrams obtained by measurements of a normal blood specimen using the reagents in Example 5.
Figure 6B:
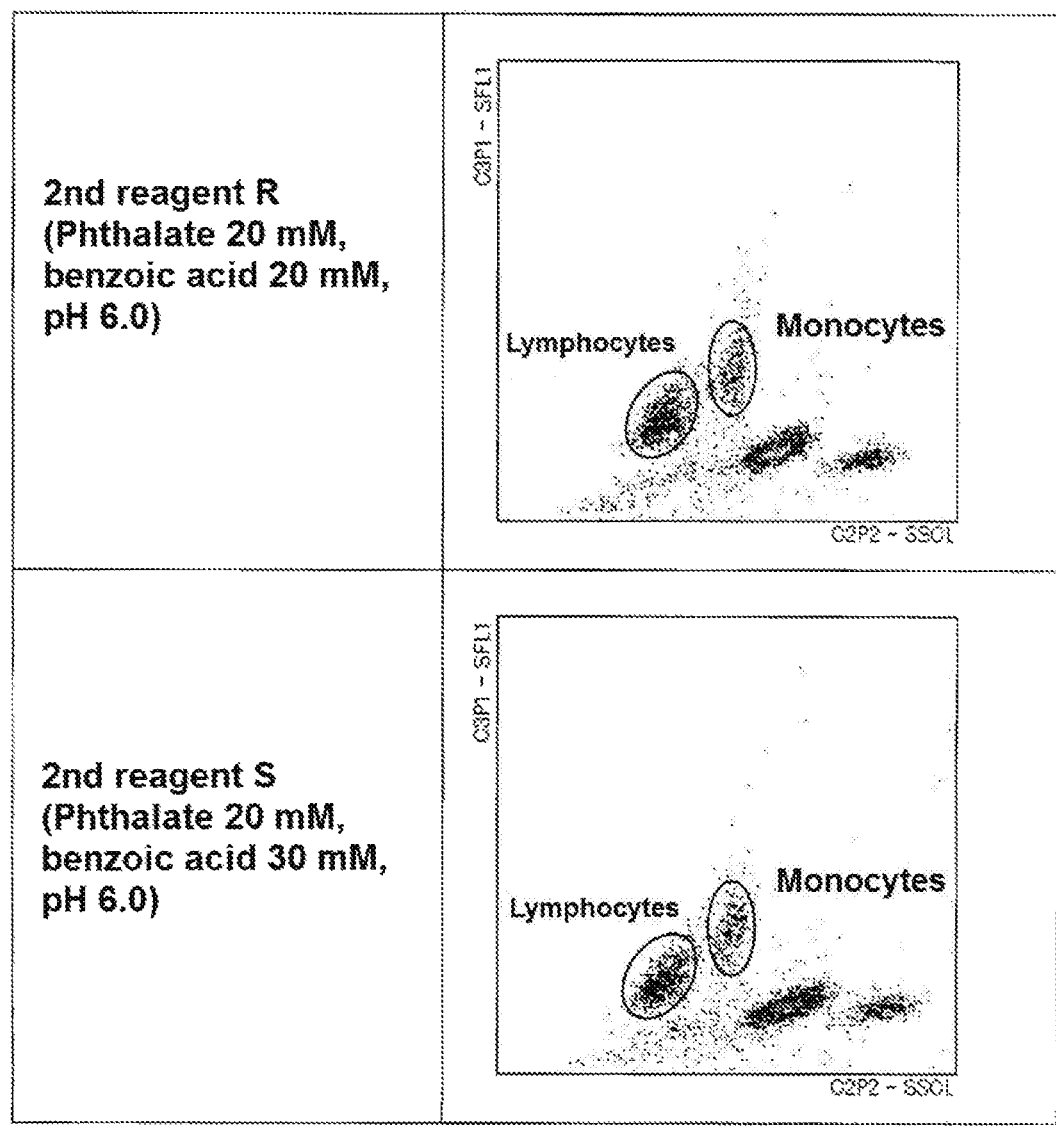

The scattergrams (X-axis: side scattered light intensity, Y-axis: fluorescence intensity) generated based on the measurements by the FCM using the reagents are shown in FIG. 6A and FIG. 6B. The centroid distance upon measurements of the specimen using the reagents and the concentration of aromatic organic acid and pH of the reagents are shown in the following Table 5.

TABLE 5

| Name of reagent | Centroid distance | Phthalate (mM) | Benzoic acid (mM) | pH |
|---|---|---|---|---|
| Second reagent A | 37.9 | 20 | 0 | 7.2 |
| Second reagent G | 44.7 | 20 | 0 | 6.0 |
| Second reagent R | 46.3 | 20 | 20 | 6.0 |
| Second reagent S | 47.0 | 20 | 30 | 6.0 |

From Table 5, FIG. 6A and FIG. 6B, it is found that the measurements with the second reagent further containing, in addition to the phthalate, benzoic acid as the aromatic organic acid can further increase the centroid distance between the cluster of monocytes and the cluster of lymphocytes.

What is claimed is:

1. A method for determining whether a biological sample contains atypical lymphocytes or myeloblasts, the method comprising the steps of:
preparing a measurement sample by mixing the biological sample with a first reagent containing a fluorescent dye capable of staining nucleic acid and a second reagent containing cationic and nonionic surfactants and an aromatic organic acid at a concentration of not less than 30 mM and not more than 50 mM, the second reagent having pH of not lower than 5.5 and not higher than 7.0,
applying light with a flow cytometer to the prepared measurement sample and obtaining side-scattered light intensity and fluorescence intensity generated thereby,
preparing a scattergram comprising the obtained side-scattered light intensity and fluorescence intensity, the scattergram having two axes of side-scattered light intensity and fluorescence intensity,
classifying the monocytes and lymphocytes on the scattergram,
and identifying a cluster of atypical lymphocytes or a cluster of myeloblasts in the prepared measurement sample,
wherein a cluster of the atypical lymphocytes is shown to deviate towards a cluster of lymphocytes on the scattergram, and a cluster of the myeloblasts is shown to deviate towards a cluster of monocytes on the scattergram.

2. The method according to claim 1, wherein the aromatic organic acid is at least one selected from the group consisting of an aromatic carboxylic acid, an aromatic sulphonic acid and a salt thereof.

3. The method according to claim 1, wherein the second reagent contains the aromatic organic acid at a concentration of not less than 40 mM and not more than 50 mM.

4. The method according to claim 1, wherein the second reagent has pH of not lower than 5.5 and not higher than 6.2.

5. The method according to claim 1, wherein the scattered light information is side scattered light information.

6. The method according to claim 1, wherein the cationic surfactant is a quaternary ammonium salt surfactant or a pyridinium salt surfactant.

7. The method according to claim 1, wherein the nonionic surfactant is a polyoxyethylene nonionic surfactant represented by the following general formula (VI):

$$R_1-R_2-(CH_2CH_2O)_n-H \qquad (VI)$$

wherein $R_1$ is an alkyl, alkenyl or alkynyl group having 8 to 25 carbon atoms; $R_2$ is an oxygen atom, —COO— or

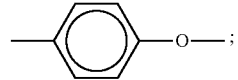

and n is an integer of 10 to 50.

* * * * *